United States Patent

Liu et al.

Patent Number: 5,195,514
Date of Patent: Mar. 23, 1993

[54] PORTABLE HAND-HELD MEDICINAL VAPORIZER

[76] Inventors: Dongfeng Liu; Hui Zhao, both of 2547 46th Ave., San Francisco, Calif. 94116

[21] Appl. No.: 871,912

[22] Filed: Apr. 21, 1992

[51] Int. Cl.$^5$ .......................................... A61M 15/00
[52] U.S. Cl. ........................... 128/203.17; 128/203.27; 392/404
[58] Field of Search ..................... 128/203.12, 203.16, 128/203.17, 203.26, 203.27, 204.15–204.17; 392/405, 406, 407, 408, 402, 404

[56] References Cited

U.S. PATENT DOCUMENTS

| | | | |
|---|---|---|---|
| 2,283,952 | 3/1939 | Robinson | 128/203.27 |
| 3,139,885 | 7/1964 | Hirtz et al. | 392/404 |
| 3,695,267 | 10/1972 | Hirtz et al. | 128/192 |
| 3,719,795 | 3/1973 | Bolomier et al. | 219/272 |
| 3,820,540 | 6/1974 | Hirtz et al. | 128/212 |
| 3,949,743 | 4/1976 | Shanbrom | 128/203.17 |
| 4,132,883 | 1/1979 | Grime | 219/284 |
| 4,338,510 | 7/1982 | Chihara et al. | 219/288 |
| 4,621,641 | 11/1986 | Frank et al. | 128/368 |
| 4,657,713 | 4/1987 | Miller | 261/142 |
| 4,739,535 | 4/1988 | Schuld et al. | 15/315 |
| 4,741,259 | 4/1988 | Ogata et al. | 99/279 |

FOREIGN PATENT DOCUMENTS 100143  1/1937  Australia ........................ 392/404

Primary Examiner—Edgar S. Burr
Assistant Examiner—Lynn D. Hendrickson

[57] ABSTRACT

A portable hand-held electric powered medicine/water vaporizer consisting of a durable plastic shell (43), lid (27) and legs (69) with sufficient operating volume to vaporize medicine/water for a short time. Inside the shell is a vessel (35) for holding medicine/water. Under the vessel is a heater (39) for heating medicine/water to generate steam. The lid (27) consists of a fixed stem (23) with an adjustable cooling extension (21) to allow the user to adjust for desired temperature and steam flow. The lower shell consists of a box for cord (59) and plug (61) storage and a stainless steel base plate (67) for stability when free standing. The base stands on four legs (69) which allows air to flow through the ventilated stainless steel base plate, to the inside of the upper shell to allow the exterior of the upper shell to remain air cooled during use. As the air passes the internal medicine/water container, it escapes the upper shell through air ports (40) located at the side of the upper shell just below the lid.

1 Claim, 6 Drawing Sheets

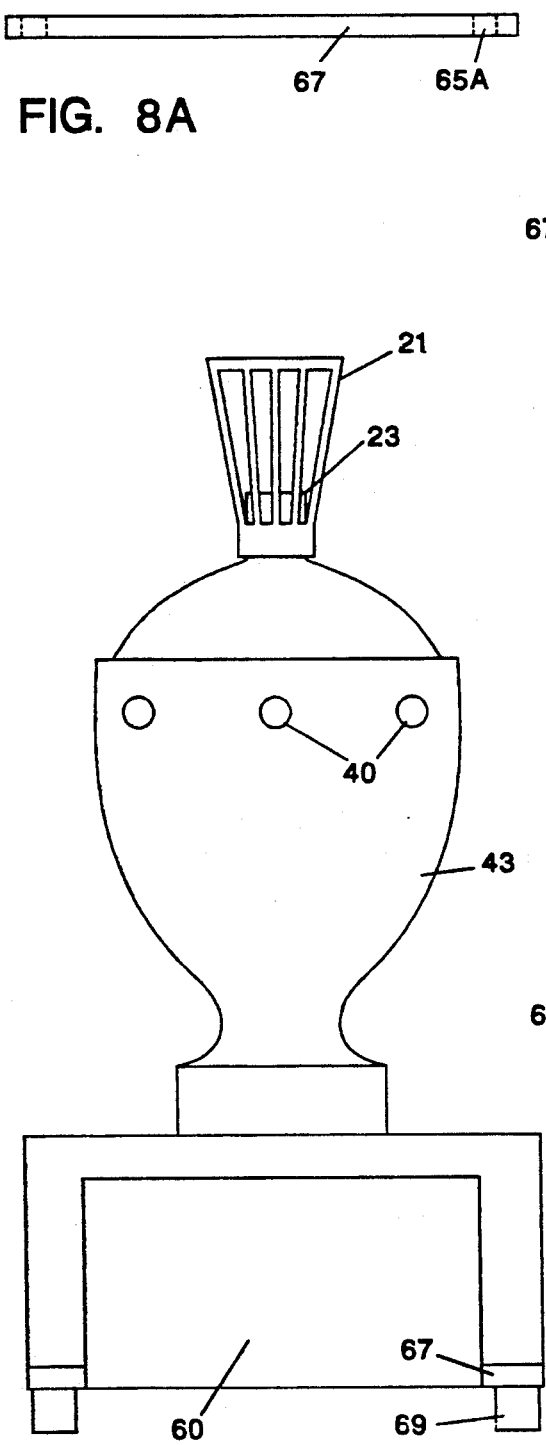
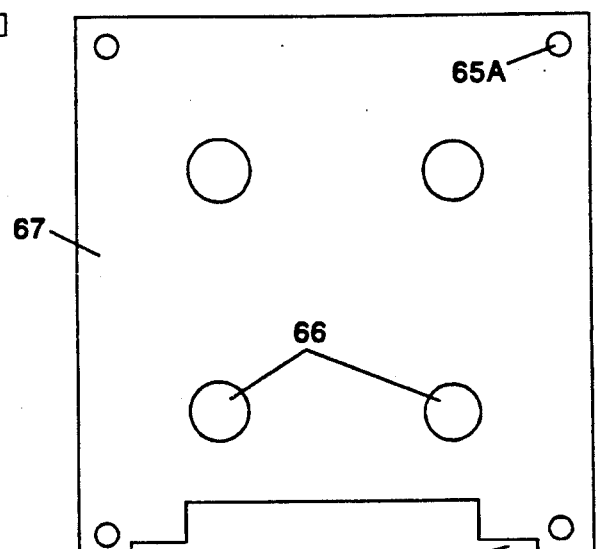
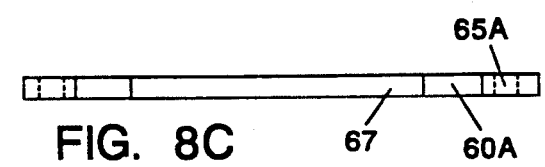
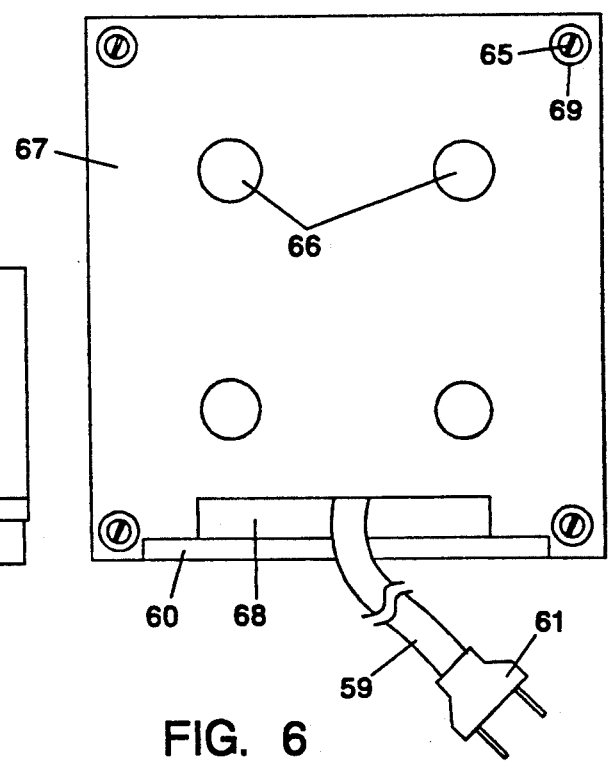

PORTABLE HAND-HELD MEDICINAL VAPORIZER

BACKGROUND

1. Field of the Invention

This invention relates generally to humidifiers/vaporizers, and specifically to an electric vaporizer for improving health and well being.

2. Prior Art

Sore and dry throats are common discomforts. Humidifiers/vaporizers are often used to turn water, which may be mixed with medication, into vapor form for inhalation. The vapor coats the throat, thereby treating and easing the discomfort. The treatment is especially effective when the vapor is medicated.

There are a whole array of humidifiers/vaporizers. Some fill the air of entire rooms with vapor so that people may breath in the medicated vapor easily. Examples of this type of humidifier/vaporizer includes U.S. Pat. Nos. 3,719,795 to Bolomier et al. (1973), 4,132,883 to Grime (1979), 4,338,510 to Chihara et al. (1982), and 4,657,713 to Miller (1987). These devices are large, bulky, and not easily transportable because they are intended for use at one specific location. They have electrical heating elements which come into direct contact with the liquid, which makes them susceptible to corrosion and therefore malfunction. In addition, they do not have vents to allow natural air circulation for cooling the interiors of their housings.

Another type of humidifier/vaporizer is small, portable, and intended for used by one person at a time. U.S. Pat. Nos. 3,695,267 to Hirtz et al. (1972) shows an inhalator for moist air. The nose piece of the device is not adjustable, while it has no provision for self support. In addition, it has a heating element which comes in direct contact with the vapor, which makes it susceptible to corrosion and malfunction. U.S. Pat. No. 4,621,641 to Frank et al. (1986) has a collapsible face mask. However, it does not provide a means for storing the power cord. Australia Patent 100,143 to Joseph Robinson (1973) shows a vaporizer which uses a cylindrical liquid container which separates the liquid from the heating element. However, its cap or nozzle is not adjustable or cooled, therefore it may not be controlled by the user. Furthermore, it has no means for storing the power cord.

These devices are either not portable, have heating elements which come into contact with the liquid, have hot nose pieces, have no means of self support, or have no means for storing the power cord.

OBJECTS AND ADVANTAGES

Accordingly, several objects and advantages of the invention is to provide an electric powered vaporizer, which is small in size, which provides a way for storing the electric cord and plug to make it very convenient to transport, which provides medicated steam, which can produce steam for use in precise locations, which separates the heating element from the liquid, which may be controlled by the user to avoid burning, which has adjustable steam output, which may be used for medical as well as beauty applications.

Further objects and advantages will become apparent from a study of the following descriptions and the accompanying drawings.

DRAWING FIGURES

FIG. 1 is a sectional view of a portable hand-held medicinal vaporizer in accordance with the invention.
FIG. 2 is a front view of the vaporizer of FIG. 1.
FIG. 3 is a top view of the vaporizer of FIG. 1.
FIG. 4A is a top view of the vessel of FIG. 1.
FIG. 4B is a side view of the vessel of FIG. 4A.
FIG. 4C is a sectional view of the vessel of FIG. 4B.
FIG. 4D is a bottom view of the vessel of FIG. 4C.
FIG. 5A is a top view of the ventilated adaptor.
FIG. 5B is a sectional view of the ventilated adaptor of FIG. 5A.
FIG. 5C is a bottom view of the ventilated adaptor of FIG. 5A.
FIG. 6 is a bottom view of the vaporizer of FIG. 1.
FIG. 7 is a rear view of the vaporizer of FIG. 1.
FIG. 8A is a front vie of the base plate of FIG. 1.
FIG. 8B is a bottom view of the base plate of FIG. 8A.
FIG. 8C is a rear view of the base plate of FIG. 8A.
FIG. 9A is a top view of the shell of FIG. 1.
FIG. 9B is a sectional view of the shell of FIG. 9A.
FIG. 9C is a bottom view of the shell of FIG. 9A.
FIG. 10 is a side view of the vaporizer of FIG. 1.

DESCRIPTION OF THE PREFERRED EMBODIMENT

Figure 4A:
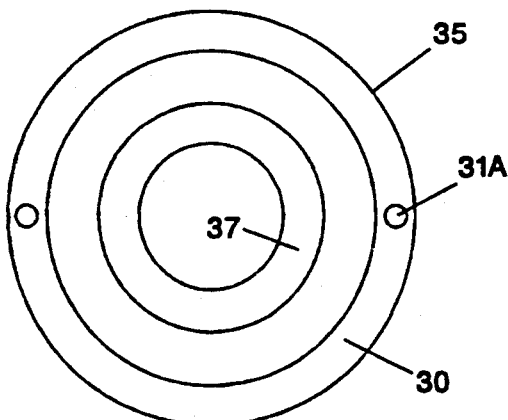
Figure 4B:
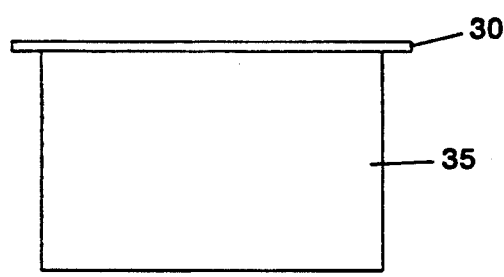
Figure 4C:
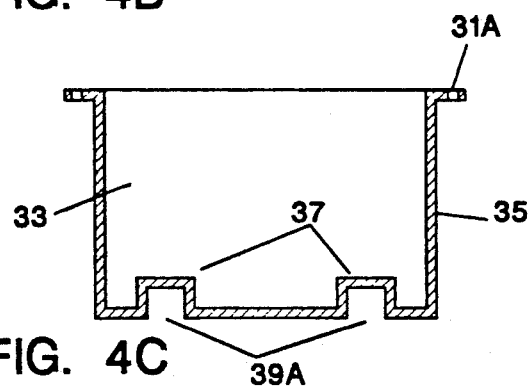
Figure 4D:
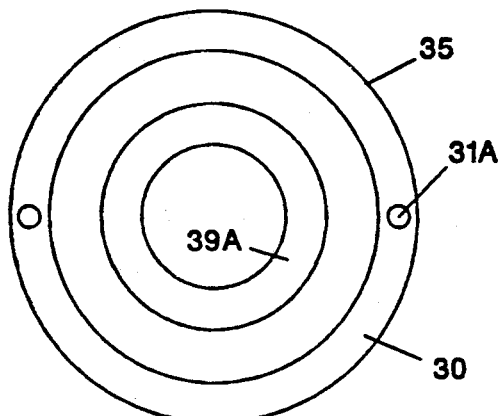
Figure 9C:
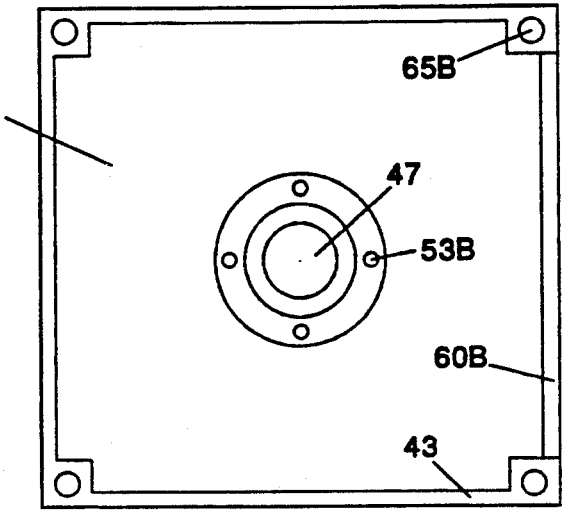
Figure 9B:
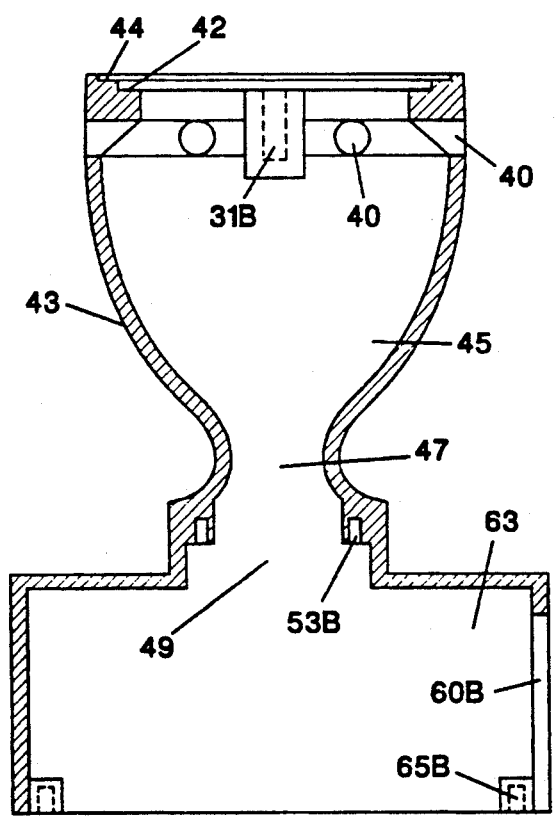
Figure 9A:
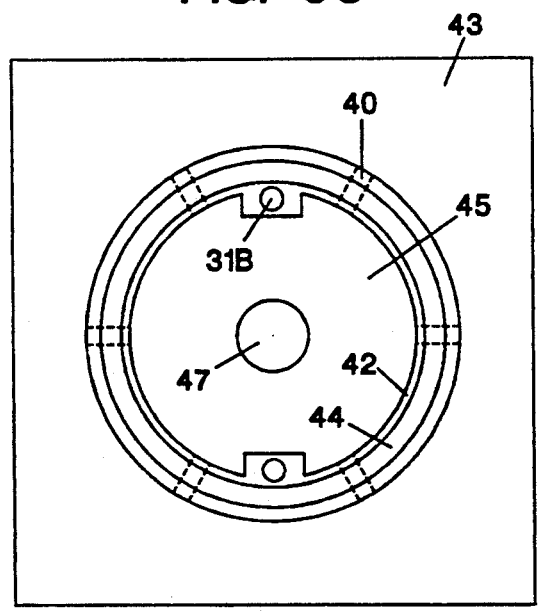

This invention can be practiced and used in many different forms. This specification and accompanying drawings disclose specific embodiments that illustrate the invention. This invention is not intended to be limited to the specific embodiments illustrated, however, In FIGS. 1, 2, 3, 4A, 4B, 4C, and 4D an adjustable cooling extension 21, which is detachable and movable upwardly and downwardly, is put on a fixed stem 23, serving as a steam outlet 25 at the central part of a lid 27 for the purpose of adjusting the desired volume and temperature of the steam during use. The fixed stem 23 at the central part of the lid 27 has a dual usage: one is to support the adjustable cooing extension 21 for a free movement on it; the other is to provide a steam outlet 25. The lid 27, made of metal, is fitted at the upper opening 44 of a shell 43 as shown in FIGS. 9A and 9B, and meanwhile it covers a vessel 35 containing water mixed with medicine so a steam chamber 29 is formed. The vessel 35, which has a liquid holding chamber 33 (FIG. 4C), is affixed to the inside part 45 of the upper shell with screws 31, which pass through screw holes 31A at the upper lip 30 of the vessel 35 and screw holes 31B near upper opening 44 (FIGS 9A and 9B). Upper lip 30 of vessel 35 rests on the groove 42 (FIGS. 9A and 9B).

An intended area 37 at the underside of the vessel 35 is adapted to accommodate a heater element 39 in a slot 39A. When an electric plug 61 is connected to the power source, AC current is passed to an electric wire 59, a connector screw 57 as well as hot wire 41, whereby the heater element 39 is heated and available for adding heat to medicine/water in the vessel 35 and convert it to steam, then the steam is discharged through the steam outlet 25.

Figure 1:
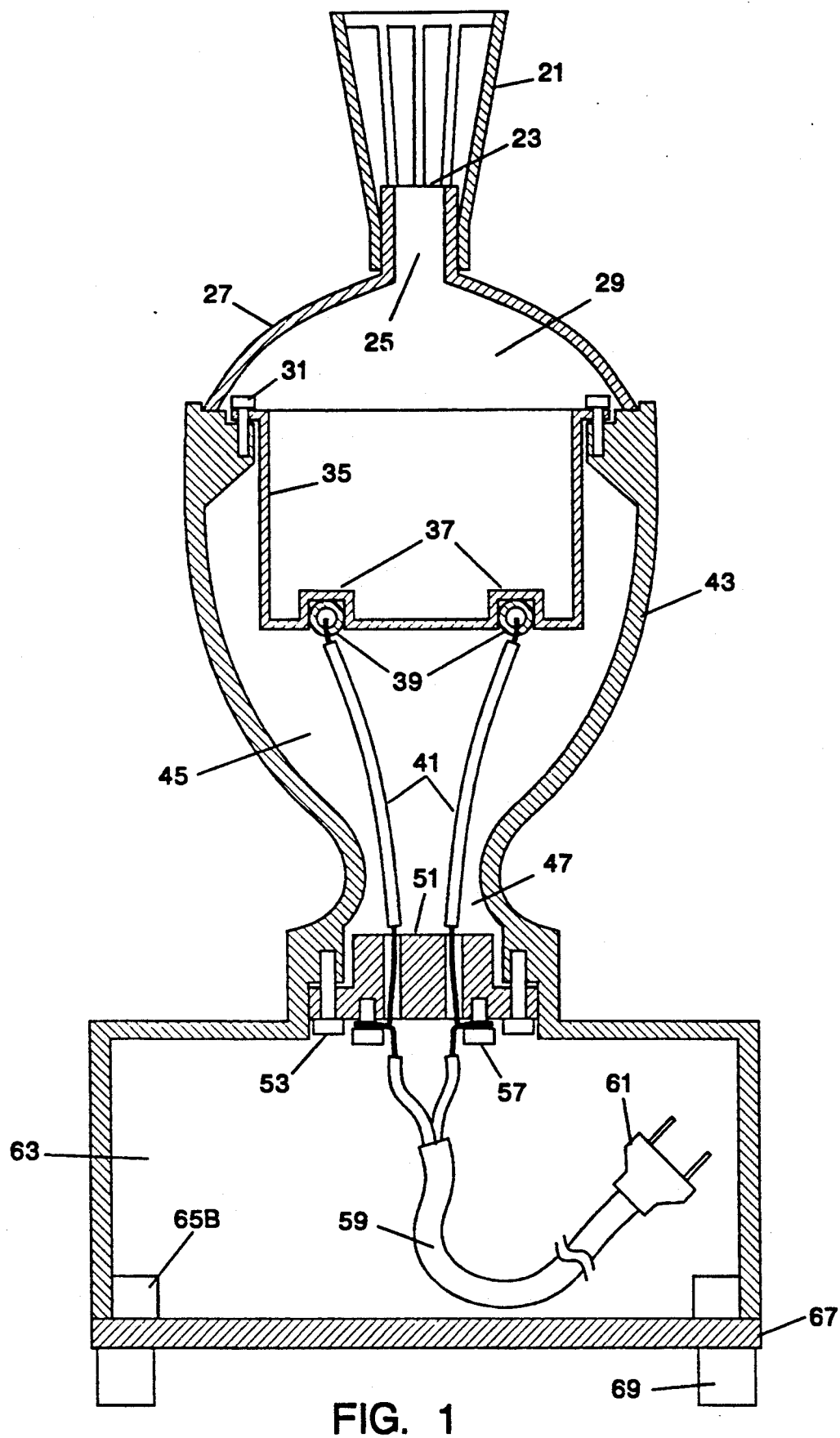
Figure 2:
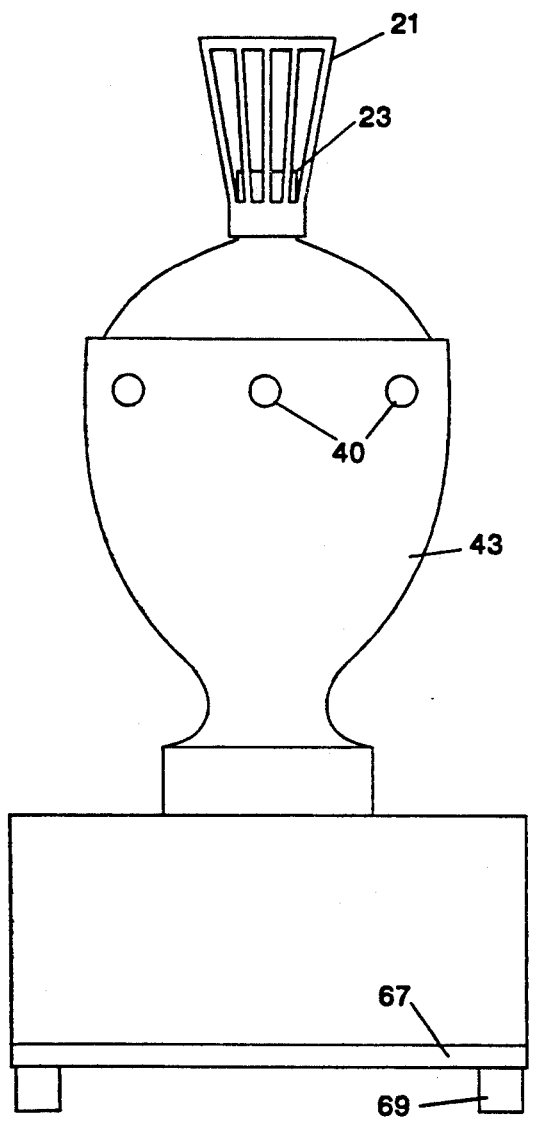
Figure 3:
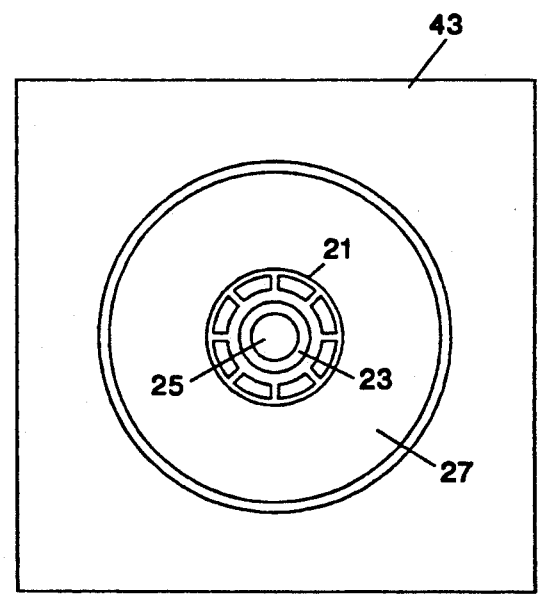
Figure 5A:
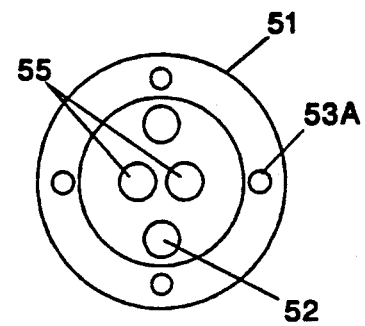
Figure 5B:
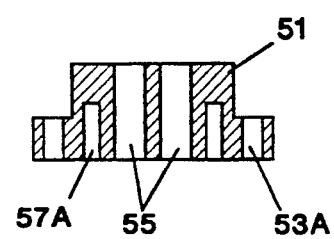
Figure 5C:
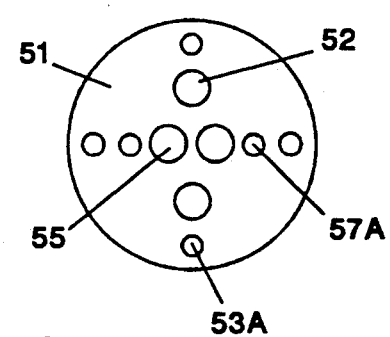

As shown in FIG. 1, a special ventilated adapter 51 is attached below throat 47 of shell 43, within a cavity 49 (FIG. 9B). Referring to FIGS. 1, 5A, 5B, 5C, 9B, and 9C, the adaptor 51 is held by screws 53 through screw passages 53A and 53B. In the adaptor 51 are central passages 55 for electrical wires 41 to pass through. As the hot wires 41 extend to the bottom of the adaptor 51, thereby the two wires, hot wires 41 and electric wire 59 are joined together by the screws 57, which extend into holes 57A of special ventilated adapter 51 (FIGS. 5B and 5C).

Figure 10:
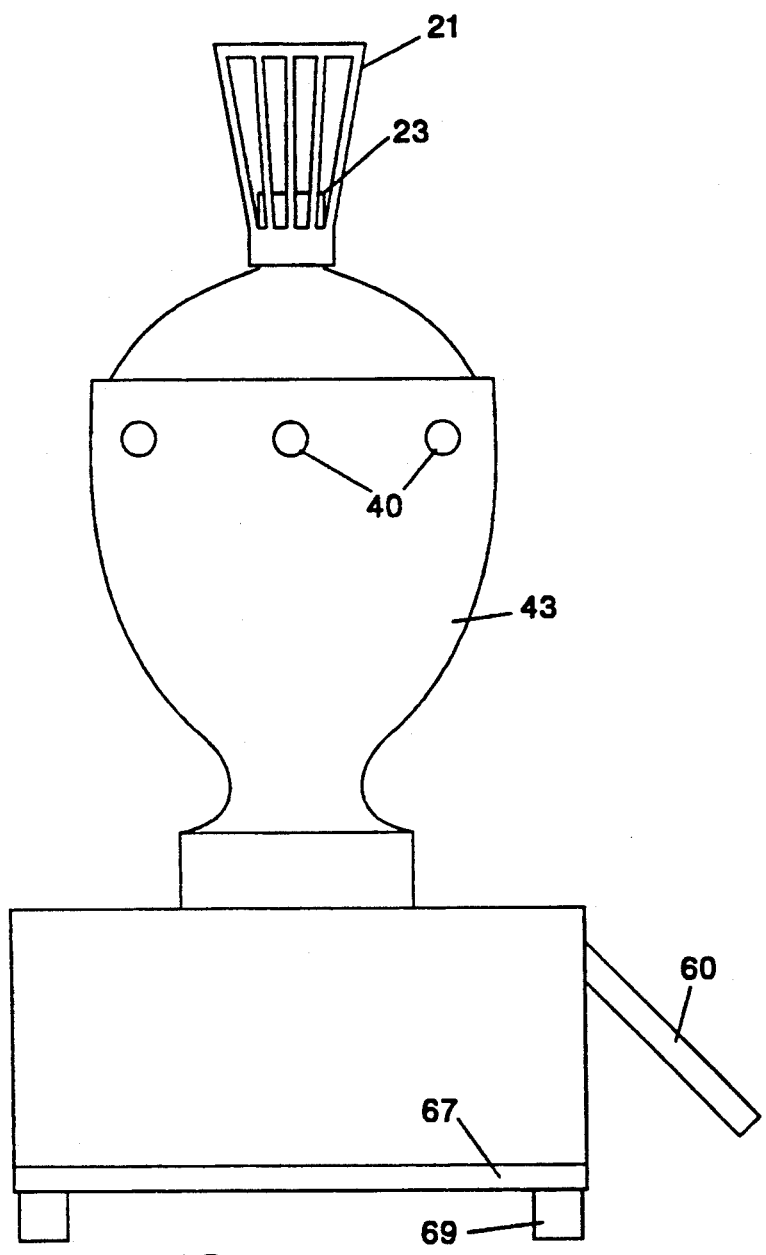

In order to keep an electric cord 59 and plug 61 in storage, a closed box 63, hereinafter referred to as a storage compartment 63, is formed by the lower portion of shell 43 and a stainless steel base plate 67. Rubber legs 69 support the entire unit and make a space for the entry of air from the bottom to the inside of the shell. The storage compartment 63 has a door 60 at the back of the unit, as shown in FIGS. 7 and 10, which swings upwardly and outwardly. The retractable electric cord 59 and plug 61 may be stored in storage compartment 63 when they are not in use, which makes the unit convenient and easy to transport.

In addition, when door 60 is closed the indented area 60A (FIGS. 8B and 8C) at one side of base plate 67 and side opening 60B of storage compartment 63 (FIGS. 9B and 9C) are covered by door 60, so an open slot 68 is formed as illustrated in FIG. 6. The slot 68, besides making it convenient for opening/closing door 60, allows the door 60 to be closed without impinging on the electric wire 59 after the wire is taken out from the storage compartment 63, and also permits the cord 59 to move freely back and forth during use. Furthermore, the open slot 69 also permits the cord 59 to move freely back and forth during use. Furthermore, the open slot 69 also works as the same function as the ventilation holes 66 providing amount of cold air to the unit.

As shown in FIG. 6, dual usage screws 65 in the base plate 67 are used to attach both the rubber legs 69 and the stainless steel base plate 67 to the inside projecting corner 65B, as shown in FIGS. 9B and C, of the storage compartment 63 by going through the passage 65A in the base plate 67 as shown in FIG. 8A, 8B, and 8C. The stainless steel base plate 67 provides weight to lower the center of gravity and enhance stability and safety.

In accordance with the present invention, according to the principle of ascending hot air up current, the portable hand-held medicinal vaporizer having high qualities of ventilation can be obtained by using a series of air ports 40, ventilation holes 66, open slot 68, and ventilation holes 52. As the base 67 stands on the four legs 69, a space is made to allow cool air to enter through the ventilated stainless steel base plate 67 to the inside of the upper shell 43. Referring now to FIGS. 2, 5A, 5C, 6, 9A, 9B, and 9C, air between legs 69 enters in through the ventilation holes 66 as well as the open slot 68 in the stainless steel plate 67 at the base, through the storage compartment 63, through the ventilation holes 52, to the interior space 45, whereby the air can be heated up between the exterior of the vessel 35 and the shell 43, when the unit is being used. Then the hot air will escape the upper shell 43 through air ports 40. Therefore, it naturally forms an air cooling system of hot/cold automatic circulation.

The foregoing discussion and illustrations are intended as examples of the present inventive concept and are not be construed as limitations hereof. Still other variations and rearrangements of ports within the spirit and scope of this invention are possible and will present themselves to those skilled in the art.

We claim:

1. A portable hand-held medicinal vaporizer comprising:
   a vessel for holding liquid,
   a lid for covering said vessel,
   a heating element attached to the outside of said vessel such that said heating element can heat said vessel and said liquid while said heating element is separated from said liquid,
   an adjustable cooling extension slidably fitted to said lid to keep the nose of the user away from said lid when said lid is hot,
   a ventilated stainless steel base plate having ventilation holes for allowing cool air to enter said vaporizer,
   a ventilated shell for housing said vessel and said heating element, said ventilated shell having air ports for allowing hot air to exit said vaporizer,
   a power cord for supplying electricity to said heating element,
   a ventilated adapter for connecting said power cord to said heating element,
   an internal storage compartment located under said vessel for storing said power cord,
   a plurality of rubber legs.

* * * * *